(12) United States Patent
Lutz

(10) Patent No.: US 6,880,790 B2
(45) Date of Patent: Apr. 19, 2005

(54) SENSOR WITH SUCTION CUP ARRAY MOUNT

(75) Inventor: Carl David Lutz, Auburn, NH (US)

(73) Assignee: Gretagmacbeth, LLC, New Windsor, NY (US)

( * ) Notice: Subject to any disclaimer, the term of this patent is extended or adjusted under 35 U.S.C. 154(b) by 0 days.

(21) Appl. No.: 10/684,853

(22) Filed: Oct. 14, 2003

(65) Prior Publication Data

US 2004/0075032 A1 Apr. 22, 2004

Related U.S. Application Data

(60) Provisional application No. 60/418,308, filed on Oct. 15, 2002, and provisional application No. 60/444,256, filed on Feb. 3, 2003.

(51) Int. Cl.⁷ .............................................. F16B 47/00
(52) U.S. Cl. .................................. 248/206.3; 356/402
(58) Field of Search ........................... 248/206.3, 206.4, 248/205.5, 363; 356/402, 218, 225, 432; 348/182, 184, 191; 250/226, 239; 345/82

(56) References Cited

U.S. PATENT DOCUMENTS

| | | | | |
|---|---|---|---|---|
| 4,671,976 A | * | 6/1987 | Vidal | 428/41.8 |
| 5,168,320 A | * | 12/1992 | Lutz et al. | 356/73 |
| 5,257,097 A | | 10/1993 | Pineau et al. | |
| 5,270,540 A | | 12/1993 | Skop, Jr. et al. | |
| 5,363,318 A | | 11/1994 | McCauley | |
| 5,739,809 A | | 4/1998 | McLaughlin et al. | |
| 5,892,585 A | | 4/1999 | Lianza et al. | |
| 6,067,166 A | | 5/2000 | Fox et al. | |
| 6,139,005 A | | 10/2000 | Nelson et al. | |
| 6,163,377 A | | 12/2000 | Boles et al. | |
| 6,260,842 B1 | | 7/2001 | Nelson et al. | |
| 6,320,652 B1 | | 11/2001 | Morimoto et al. | |
| 6,459,425 B1 | | 10/2002 | Holub et al. | |
| 6,459,485 B1 | | 10/2002 | Tsurutani | |
| 6,526,618 B1 | * | 3/2003 | Bolton | 15/160 |
| 6,611,249 B1 | * | 8/2003 | Evanicky et al. | 345/102 |
| 2002/0085197 A1 | * | 7/2002 | Slocum et al. | 356/220 |
| 2003/0058202 A1 | | 3/2003 | Evanicky et al. | |
| 2003/0058448 A1 | | 3/2003 | Merle et al. | |
| 2004/0080749 A1 | * | 4/2004 | Lutz et al. | 356/405 |
| 2004/0114041 A1 | * | 6/2004 | Doyle et al. | 348/182 |
| 2004/0114144 A1 | * | 6/2004 | Lutz et al. | 356/419 |

FOREIGN PATENT DOCUMENTS

GB     2314263 A   * 12/1997    E03C/1/264

OTHER PUBLICATIONS

"Monaco OPTIX", 2002, pp. 1–2, Monaco Systems, Inc., Andover, MA.

"Monaco Systems, Inc.– Color Management", http://www.monacosys.com/, 2002, p 1, Monaco Systems, Inc., Andover MA.

(Continued)

*Primary Examiner*—Ramon O Ramirez
(74) *Attorney, Agent, or Firm*—Maine & Asmus

(57) ABSTRACT

A sensor mounting system having a suction cup array is disclosed. In one application, the system eases the initial positioning of the calorimeter on the screen to be measured, minimizes the force applied to the screen upon which it is mounted, and minimizes the distortion in the mounted area of the screen surface. In addition, the mounting system can be configured so that the distance from the colorimeter sensor to the screen will not significantly change over time. Such positional stability operates to improve SNR. The mounting system is further adapted for ease of removal from the screen upon which it is mounted. Applications not only include a mount for low to high accuracy calorimeters, but also for other measurement devices that can benefit from advantages of the present invention. Injection molding manufacturing techniques can be employed in fabrication of the system.

21 Claims, 8 Drawing Sheets

OTHER PUBLICATIONS

"iProfile Bundle: One Big Package. One Small Price", 2000, pp. 1–4, Gretag–Macbeth Holding AG., Regensdorf, CH.

"Monaco OPTIX", 2003, pp. 1–2, Monaco Systems, Inc., Andover, MA.

"Monacooptix With "Light Tunnel" Technology for Accurate LCD and CRT Display Profiling Now Available", http://www.monacosys.com/, 2002, p 1, Monaco Systems, Inc., Andover MA.

Briot, A. "Calibrating & Profiling LCD Displays Using ColorBlind ProveIt", http://www.luminous–landscape.com/tutorials/acd–profile.shtml, pp. 1–7, 2002.

Rodney, A. "CMS Redux: Color Management System Hardware and Software Get More Sophisticated and Often, Easier to Use", PEI, Sep. 2000, pp. 22–28.

"NEC–Mitsubishi Electronics Displays Enhances Award Winning Line of CRT Monitors for Color Preference Users", www.necus.com/companies/17/Enhance_crt_color_users.htm, pp1–3, 2001.

"Spectrolino Spectrophotometer", GretagMacbeth, pp. 1–4, 1998.

Fraser, B. "The Color Challenge: Can Flat–Panel Displays Replace CRTs on Publisher's Desks?", MacWorld, www.macworld.com/2001/06/features/color, pp. 1–7, Jun. 2001.

"Spyder: Professional Quality On–Screen Color", pp. 1–6, 2003, ColorVision, Inc., Lawrenceville, NJ.

Lyons, I.,"Monitor Calibration & Profiling: PhotoCAL and OptiCal" Computer–Darkroom, http://www. computer-darkroom.com/photocal/photocal_1.htm, pp. 1–8, Dec. 7, 2002.

Related products including some of the features of the present invention may have been offered for sale more than one year before the effective filing dates of this application.

Some claimed embodiments of the present invention may have been offered for sale, but not more than one year before the filing date of Provisional application No. 60/418,308, to which priority is claimed.

PCT International Search Report dated Jul. 27, 2004 of International Application No. PCT/US03/32834 filed Oct. 15, 2003.

* cited by examiner

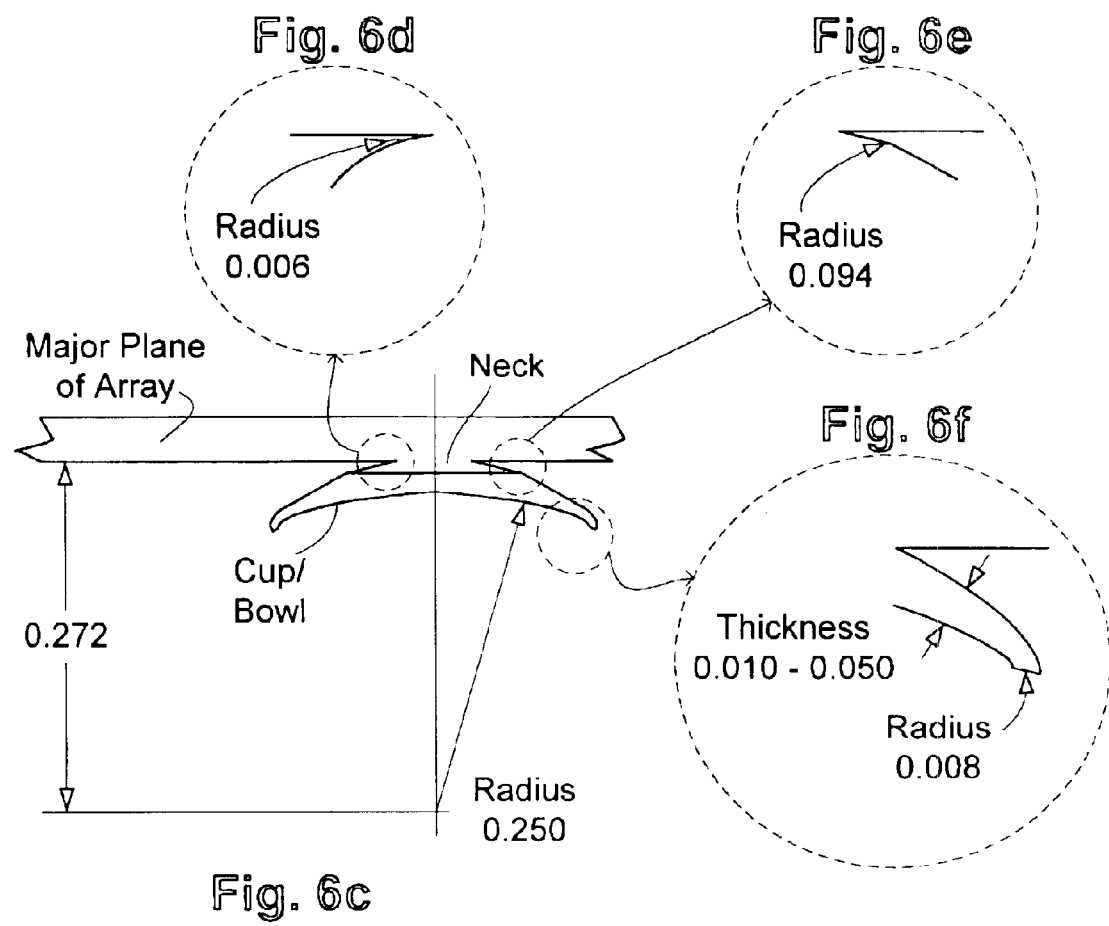

SENSOR WITH SUCTION CUP ARRAY MOUNT

RELATED APPLICATIONS

This application claims the benefit of U.S. Provisional Application Nos. 60/418,308, filed 15 Oct. 2002, and 60/444,256, filed 3 Feb. 2003. Each of these applications is herein incorporated in its entirety by reference. In addition, this application is related to U.S. application Ser. No. 10/684,864, filed Oct. 14, 2003, titled "Colorimeter with High SNR" and to U.S. application Ser. No. 10/684,854, filed Oct. 14, 2003, titled "Colorimeter with Single Cable Low Impact Mounting System". Each of these applications is herein incorporated in its entirety by reference.

FIELD OF THE INVENTION

The invention relates to techniques for mounting sensors to surfaces, and more particularly, to a colorimeter configured with a suction cup array mount.

BACKGROUND OF THE INVENTION

Measurement instrumentation often involves the mounting of a sensor to a surface to be measured. The parameters to be measured vary with the field of interest and sensing transducer employed, yet common to many applications is the need to mechanically affix or position a sensor to a non-porous surface to be measured. For specialized conditions the sensor (such as a strain gauge) can be bonded directly to the surface to be measured. For many cases, however, the surface must be undisturbed after measurement. Such is the case of measurement of computer displays measured by colorimeters.

Colorimeters are devices for measuring the spectral content of light, where the measured light can be emitted either directly or indirectly from a given source. Recent developments have produced designs resulting in low cost colorimeters with performance characteristics approaching or exceeding professional quality required by the standards. One such colorimeter design is described in detail in U.S. Pat. No. 5,892,585, which is herein incorporated by reference in its entirety. With such cost effective, high-performance colorimeter designs available, a need has arisen for techniques for effectively mounting the colorimeter to the device being measured. In more detail, the physical factors relating to mounting a calorimeter to a target device present a number of non-trivial problems.

For instance, it is necessary to ensure that the forces of attachment are minimized to reduce pressure applied to a computer having a liquid crystal display (LCD). Otherwise, color distortion or damage to the LCD will occur. Also, LCD screens are particularly sensitive to the distribution and magnitude of the mounting forces. Thus, it is desirable that the calorimeter be relatively easy to position and attach to the target device. In addition, it is necessary to shield the measuring system from extraneous light (light from sources other than the target device being measured), which will otherwise reduce the signal-to-noise (SNR) ratio of the calorimeter system.

One conventional calorimeter design employs a strap or hanging apparatus for securing or otherwise suspending the colorimeter in front of a display screen. A donut-shaped foam pad or similar soft pad is used to keep the colorimeter from pressing too hard on the screen so as to prevent color distortion. However, such designs are cumbersome to use due to the nature of the strap or hanging apparatus, and generally provide a significant impediment to simple user operation. Moreover, such designs may not operate to maximize the SNR of the colorimeter device, particularly those designs where the colorimeter's peripheral field of view is not limited.

Other conventional designs employ one to four relatively large suction cups to hold the calorimeter in place. One such device uses a large annular suction cup fitted about a color sensor, where the sensor measures through the center. Another such design uses a large rubber suction cup with a rigid clear member through which a proximate sensor can measure. Another such embodiment employs four large suction cups, one at each corner of the sensing device. These suction cup methods each suffer from reliability issues.

For example, if the seal fails due to an imperfection in materials or a particle of dust or debris, then air will leak into the cavity causing that suction cup to fail. With just one suction cup, the device will simply fall off the target being measured. With the four corner type design, the weight of the device will be unevenly distributed, thereby causing a shift in alignment of the device and/or the failure of the remaining seals. This problem is further exacerbated in that displays have a tendency to attract dust. Moreover, the suction cups used in such designs have a relatively large depth. As a result, a slow air leak will cause the distance between the screen and sensor to substantially increase, thereby adversely affecting device measurement accuracy.

What is needed, therefore, are improved techniques for mounting a colorimeter to a target screen.

BRIEF SUMMARY OF THE INVENTION

One embodiment of the present invention provides a mounting system for attaching a sensor (such as a colorimeter) to a target screen. The system includes an array of suction cups adapted to hold the sensor in position on the target screen. Each cup in the array has a maximum displacement distance of 0.115 inches or less, thereby enabling positional stability of the sensor. The maximum displacement distance defines a distance any one cup will move in transitioning from a fully engaged-state to a fully relaxed-state. A baseplate is operatively coupled to the array of suction cups, wherein the baseplate is adapted to be operatively coupled to a housing of the sensor or is part of the sensor housing. The array of suction cups can be, for example, a single piece of injection moldable elastomer or rubber. Also, the array can be integral with the baseplate, or can alternatively be bonded to the baseplate.

In one such embodiment the sensor is a colorimeter, and the system further includes a sensor hole located in the array that allows sensors of the calorimeter to receive light emitted from the target screen, and a sensor shield located about the sensor hole. This shield is adapted to shield sensors of the colorimeter from extraneous light generated by sources other than the target screen. The sensor shield can be formed, for example, as an integral part of the array using injection molding techniques. In another such embodiment, the system further includes one or more rigid stops located on the array, so as to establish a pre-set distance of the colorimeter to the target screen. Each stop has a height that allows each of the suction cups to be fully seated. Note that the one or more rigid stops can also be formed as an integral part of the array using injection molding techniques.

The array may include, for example, an inner group of suction cups and an outer group of suction cups, and be a single piece of injection moldable elastomer or rubber. In such a case, the inner and outer groups of suction cups can each be arranged in respective rings, with each group having ten or more suction cups each having a maximum diameter of 0.250 inches or less. The number of cups, as well as the cup dimensions, can be selected given the particulars of the application (such as the weight of a colorimeter to be mounted, the type of target surface, and the desired/acceptable force required mounting and removing the system from the target screen).

Another embodiment of the present invention provides a mounting system for attaching a calorimeter to a target screen at a pre-set distance. The system includes an injection molded array of suction cups adapted to hold the colorimeter in position on the target screen, and to control both the pre-set distance and variation of distance between the colorimeter and the target screen. The array includes an inner group of suction cups and an outer group of suction cups. Also includes is a sensor hole located in the array, so as to allow sensors of the colorimeter to receive light emitted from the target screen, and a sensor shield located about a sensor hole located in the array. The sensor shield is adapted to shield sensors of the calorimeter from extraneous light generated by sources other than the target screen. Note that the array, sensor hole, and sensor shield can be fabricated as a single piece of injection moldable elastomer or rubber.

In one such embodiment, the array includes one or more rigid stops that operate to establish the pre-set distance of the calorimeter to the target screen. Each stop has a height that allows each of the suction cups to be fully seated. Each cup in the array can have, for example, a maximum displacement distance of 0.115 inches or less, thereby enabling positional stability of the colorimeter. In addition, each suction cup can have, for instance, a maximum cup diameter of 0.250 inches or less. The system may further include a baseplate that is operatively coupled to the array of suction cups, wherein the baseplate is adapted to be operatively coupled to a housing of the colorimeter or is part of the colorimeter housing. In one such embodiment, the baseplate is rigid and the system further includes a pull tab operatively coupled to one end of the baseplate and a pivot point at an opposite end, thereby allowing the mounting system to be cantilevered off of the target screen during removal.

Another embodiment of the present invention provides a mounting system for attaching a device to a target surface. The system includes an array of suction cups adapted to hold the device in position on the target surface, each cup in the array having a maximum displacement distance of 0.115 inches or less, thereby enabling positional stability of the device. The system further includes one or more rigid stops that operate to establish a pre-set distance of the device to the target surface, with each stop having a height that allows each of the suction cups to be fully seated. Each suction cup can have, for example, a maximum cup diameter of 0.250 inches or less.

As will be understood in light of this disclosure, the device can be a colorimeter and the target surface can be a screen (e.g., LCD screen). In such a case, the system may further include a sensor hole and shield as previously stated. Note that the array, the sensor shield, and the one or more rigid stops can be a single piece of injection moldable elastomer or rubber.

The system may further include a baseplate that is operatively coupled to the array of suction cups, wherein the baseplate is adapted to be operatively coupled to a housing of the device or is part of the device housing. In one such case, the baseplate is rigid and the system further includes a pull tab operatively coupled to one end of the baseplate and a pivot point at an opposite end, thereby allowing the mounting system to be cantilevered off of the target surface during removal.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

BRIEF DESCRIPTION OF THE DRAWINGS

FIG. 1b is a cross-section view of the colorimeter mounting scheme shown in FIG. 1a.

FIG. 2b is a cross-section view of the colorimeter mounting scheme shown in FIG. 2a.

FIG. 3b is a cross-section view of the colorimeter mounting scheme shown in FIG. 3a.

FIGS. 6a–c illustrate dimensional details of a colorimeter mounting scheme configured in accordance with one embodiment of the present invention.

Figure 3A:
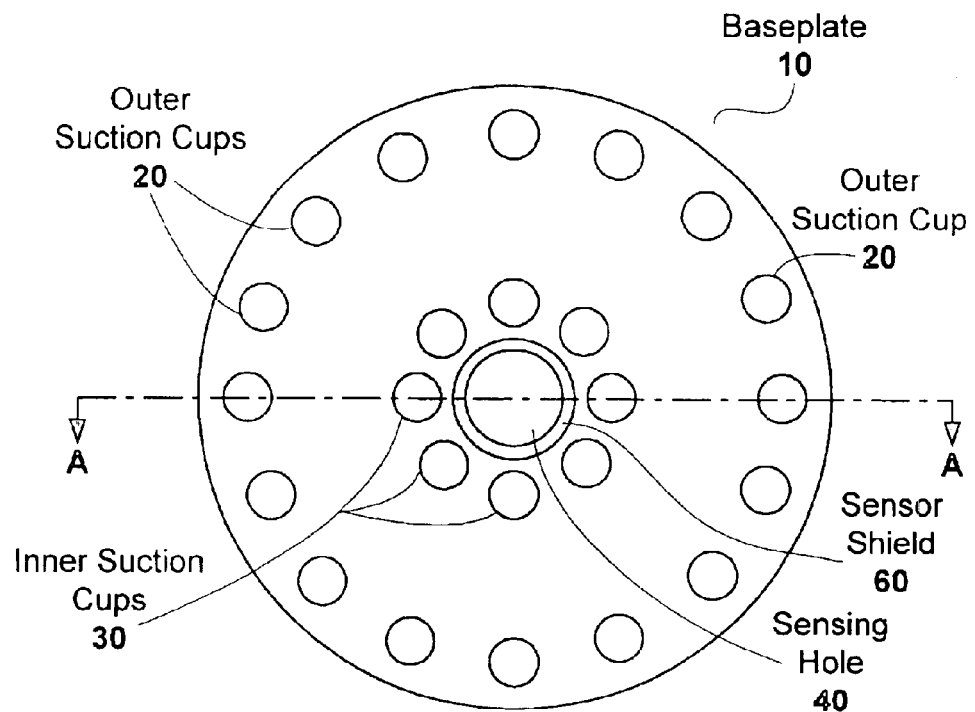
FIG. 3a is a bottom view of a colorimeter mounting scheme configured in accordance with another embodiment of the present invention.
Figure 3B:
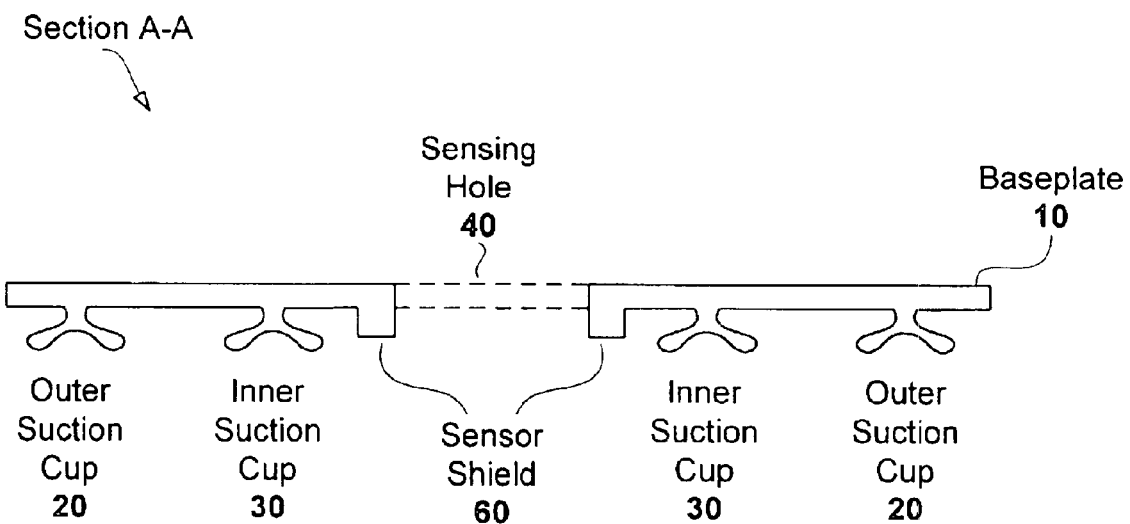
Figure 4:
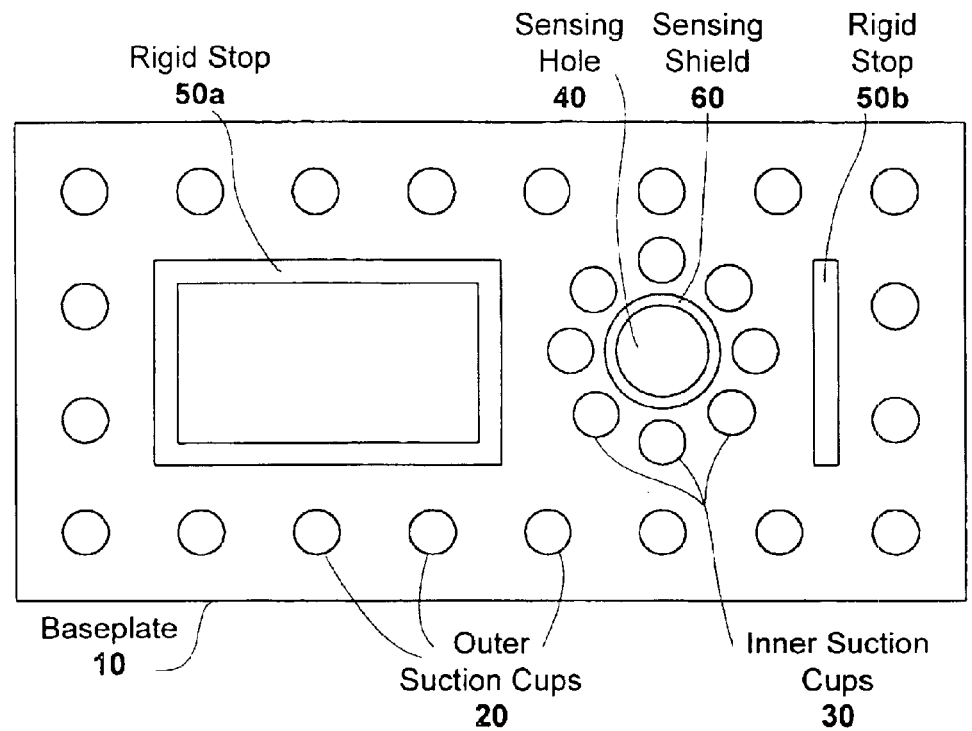
FIG. 4 is a bottom view of a colorimeter mounting scheme configured in accordance with another embodiment of the present invention.

Note that the figures are presented to facilitate understanding and clarity of individual features, and are not necessarily drawn to scale. Further note that like reference labels in different figures refer to like features. Feature characteristics such as shape and size may vary from one embodiment to the next, but the general feature will be apparent in light of the disclosure. For example, the baseplate 10 in FIGS. 3a and 3b is round, while the base plate 10 in FIG. 4 is rectangular.

DETAILED DESCRIPTION OF THE INVENTION

Embodiments of the present invention provide a mounting system for screen mounted calorimeters capable of measurement of emitted light from sources that are static (e.g., LCD displays, illuminated printed or graphic matter) and/or temporally active (e.g., CRT displays or strobed printed and graphic matter). The mounting system minimizes or otherwise removes factors that contribute to undesirable results, including changes in the mounting distance (calorimeter body to screen) over time. In addition, the mounting system enables the distribution of mount forces so as to not distort the screen output in the mount area or damage the screen, as well as to afford ease of removal of the calorimeter from the screen.

Positional stability of mounting system is achieved by using an array of pliable, small suction cups. Each suction cup has a shallow bowl to facilitate a short displacement distance and positional stability of the mount. The overall array enables distribution of the mounting force to minimize or otherwise eliminate screen distortion. In addition, the mounting system requires a relatively low attachment force, thereby enabling easy positioning of the device, as well as ease of device removal. Thus, a light measurement system is enabled that can be readily mounted to a target device, and that can maintain desired measurement accuracy requirements.

A mounting system configured in accordance with the principles of the present invention can include other features as well, such as the ability to stick or otherwise adhere to a number of target surface types, including nonporous, smooth surfaces such as glass, and the ability to leave no residue on the mounted surface once the mount is removed. In addition, the mounting system disclosed herein contributes to device performance repeatability, since a fixed or otherwise stable mount distance can be maintained with a pre-defined distance between the device being measured and the mounting system. This stability further contributes to low cost and complexity, as optical lenses and/or other componentry used by conventional devices to compensate for variations in mounting distance can be eliminated.

It will be appreciated in light of this disclosure that the principles of the present invention can be applied to applications other than the mounting of calorimeters, and in particular, wherever highly stable and repeatable, low-damage-impact mounting techniques are beneficially employed or otherwise desired.

Structural Features of Mounting System

FIGS. 1a through 5 demonstrate various structural features of a mounting system configured in accordance with the principles of the present invention. Numerous configurations and embodiments will be apparent light of this disclosure, and any of the various features may be employed alone or in combination for a particular configuration. Thus, it will be appreciated that the invention is not intended to be limited to the illustrated example embodiments.

Figure 1A:
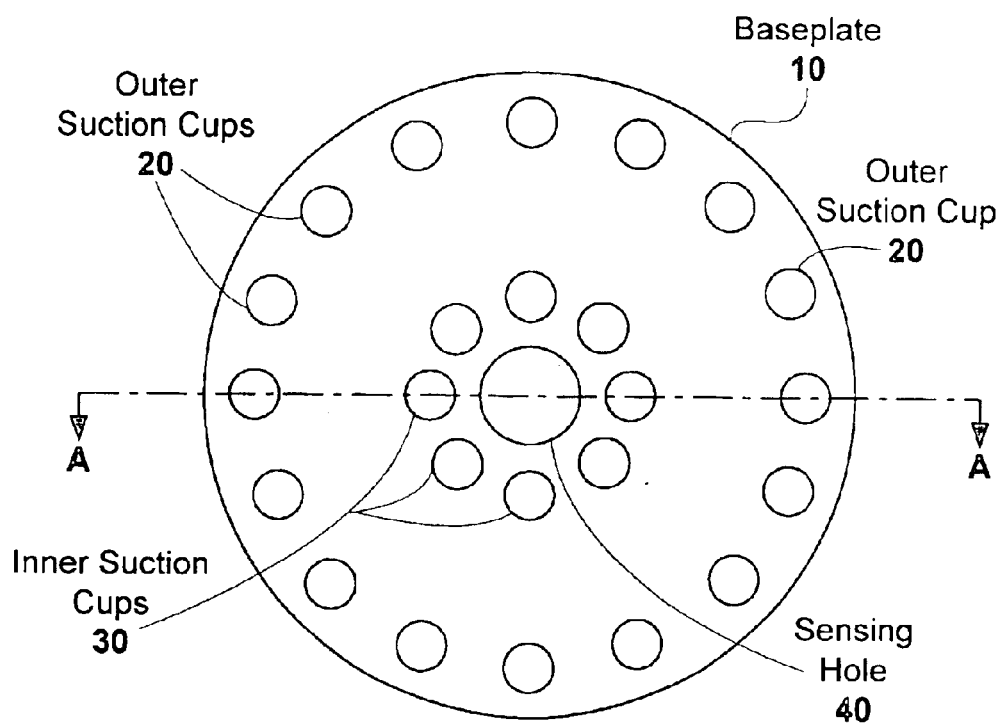
FIG. 1a is a bottom view of a calorimeter mounting scheme configured in accordance with one embodiment of the present invention.
Figure 1B:
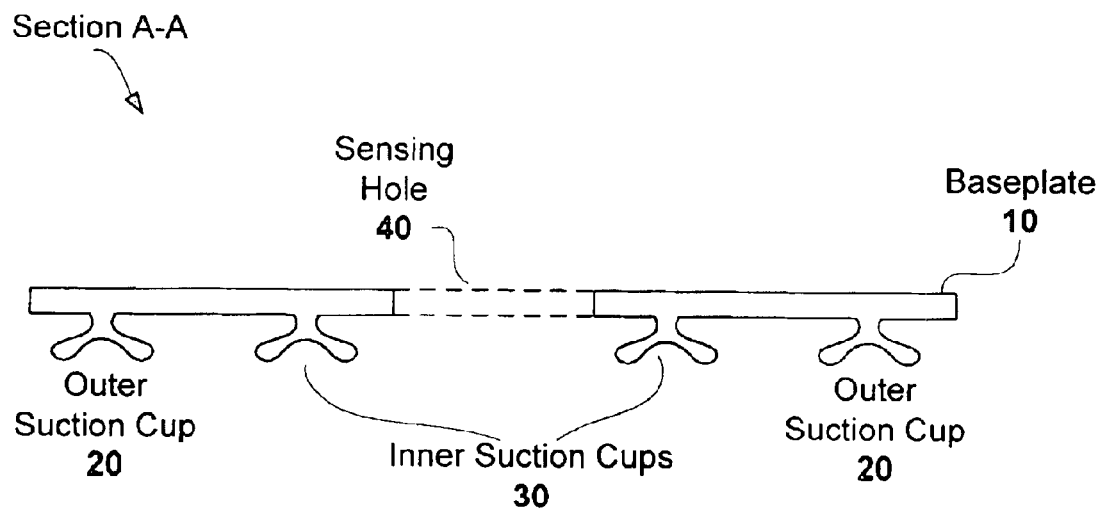
Figure 1C:
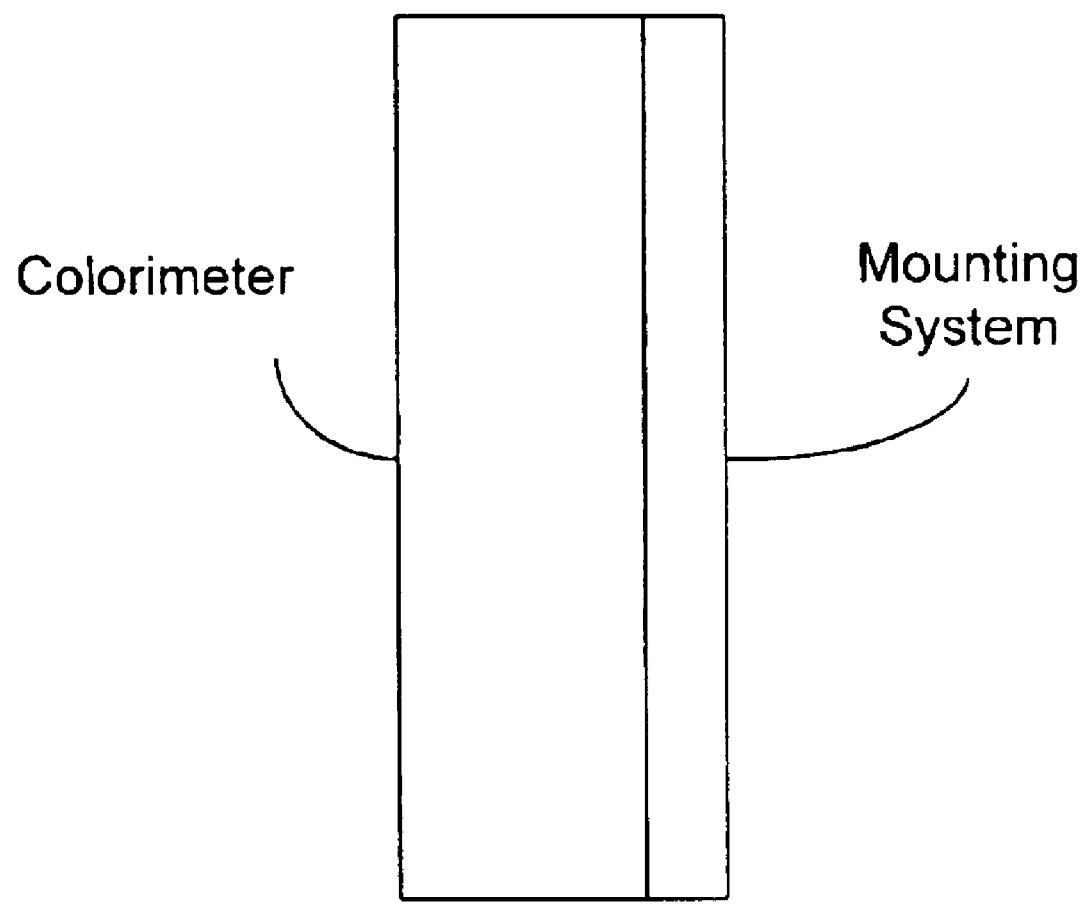
FIG. 1c is a side view of the colorimeter mounting scheme shown in FIG. 1a coupled with a colorimeter.

FIGS. 1a and 1b and 1c provide respective views of a colorimeter mounting scheme configured in accordance with one embodiment of the present invention. As can be seen, the mounting system includes a baseplate 10, a set of outer suction cups 20, a set of inner suction cups 30, and a sensing hole 40. Other componentry and features, such as a window pane over the sensing hole 40, and a power cord, may also be included. For purposes of discussion, assume that the mounting system is operatively coupled with a colorimeter as shown in FIG. 1c. However, other devices could be coupled with the mounting system as well.

Figure 7:
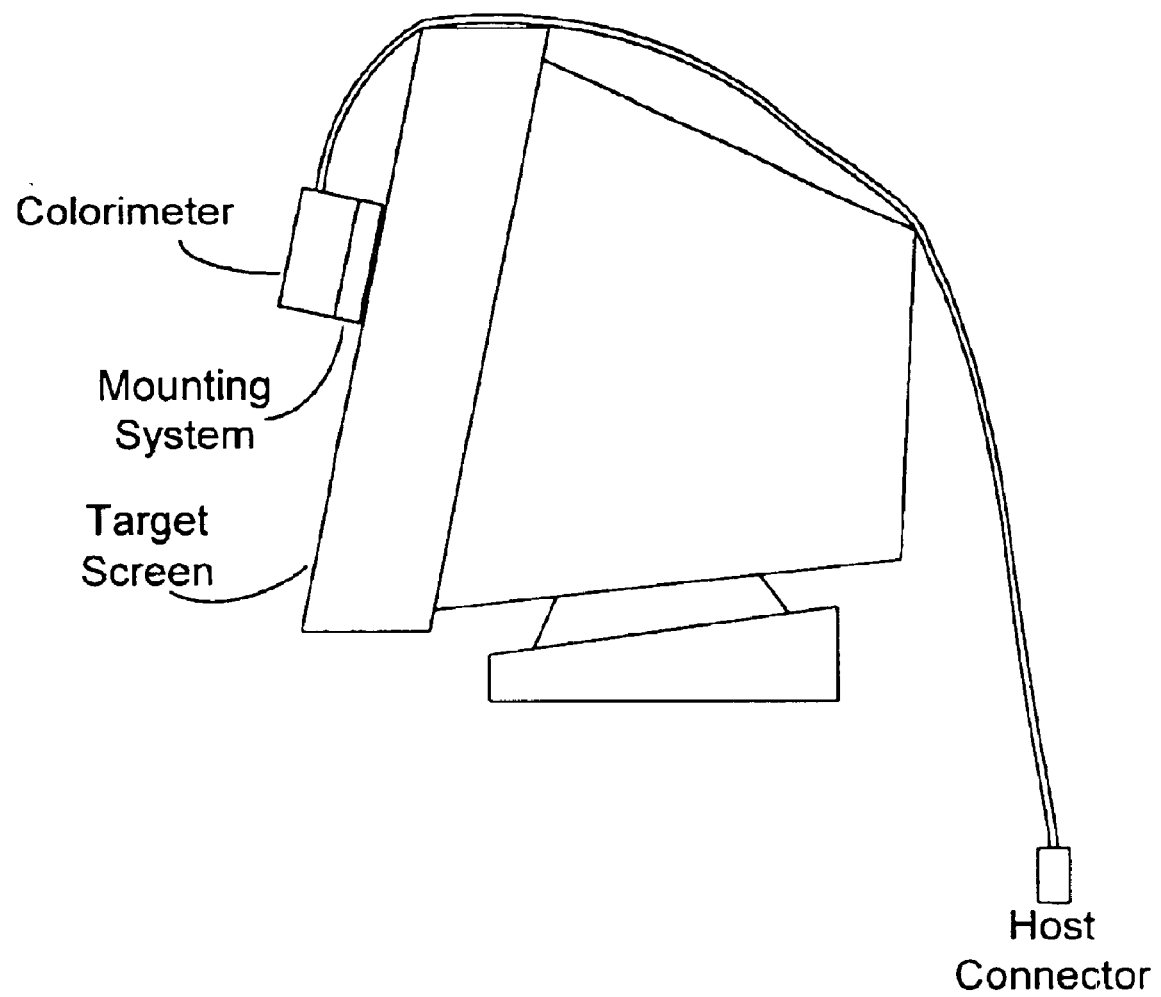
FIG. 7 is a side view of a colorimeter mounting scheme coupling a colorimeter to a target screen, in accordance with an embodiment of the present invention.

The colorimeter can be implemented in conventional technology, and includes a sensor that is adapted to receive light emitted from a target source via the sensing hole 40. In one particular embodiment, the colorimeter is configured as described in U.S. Pat. No. 5,892,585, although other colorimeters can be used here as well. The mounting system allows the colorimeter to be mounted to the surface of an electronic display, computer screen, or TV (as shown in FIG. 7) while measurements of the light displayed on the display, screen or TV are conducted. Measurements include, for example, luminance and chromaticity, as well as other parameters.

The baseplate 10 is configured with a suction cup array including a number of suction cups arranged in a desired pattern. In this case, the selected pattern includes a ring of outer suction cups 20 and a ring of inner suction cups 30. The sensing hole 40 is cut through the baseplate 10 and aligns to the sensing window of the calorimeter. The configuration (e.g., shape, location of sensing hole) of the baseplate 10 can generally be adapted to accommodate the colorimeter or other device that is being mounted. In this case, the circular shape of the baseplate 10 and the inner and outer suction cup groups 20/30 can be attributed to a circular-shaped calorimeter. It will be apparent in light of this disclosure, however, that other shapes for the base plate and suction cup array pattern are possible.

In one particular embodiment, the baseplate 10 and the inner and outer suction cup groups 20/30 are fabricated as a single molded piece of injection moldable elastomer or rubber. Here, the suction cup array formed from the baseplate 10 with the inner and outer suction cup groups 20/30 can be integrally-molded or over-molded as part of the colorimeter housing. Alternatively, the baseplate 10 can be a rigid piece of metal or plastic cut to an appropriate shape, and a suction cup array formed with the inner and outer suction cup groups 20/30 can be a single injection molded construction of elastomer or rubber. This separately fabricated suction cup array can be coupled with the baseplate 10 using an adhesive or other suitable fastening mechanism. The combined assembly can then be fastened to the colorimeter housing. Alternatively, the rigid baseplate 10 can be integral to the housing of the calorimeter, and the separately fabricated suction cup array can be coupled accordingly.

Material ALCRYN 2260 is one example of a thermoplastic elastomer which is injection moldable, and can be used to form the baseplate and or suction cup array. This rubber-like material blend is well-suited to achieve low viscosity requirements during molding while supplying desired material properties. LOCTITE 401 and Prism primer are example adhesives that can be used to bond the suction cup array to a rigid support piece or device housing made from, for example, ABS/PC plastics. Note that the mounting system can be integral to the colorimeter or other mountable device having similar mounting requirements.

A suction cup array configured in accordance with the principles of the present invention provides many smaller cups for a more distributed and reliable suction. If one fails or leaks, many more still ensure proper distribution of the related forces with no overall failure. In addition, injection molding a single piece provides many operable suction cups at the cost of one part. Also, because each cup of the array is small in diameter and not too deep, the movement (relative to a target surface) associated with transitioning from an engaged-state to a relaxed-state for any given cup is relatively short. Thus, even if the mounting system relaxes a bit, the change in mounting distance is short compared to conventional techniques that employ one to four larger suction cups.

Also, the suction cup array is configured to require a low removal force so that it is easy to peel off or otherwise remove from the target surface of the device under test. In more detail, the multitude of suction cups need not be removed all at once, but rather can be removed in a more singular fashion by essentially peeling the edge of the suction cup array off the target surface. Additional dimensional details of the suction cup array architecture will be discussed in more detail in reference to FIGS. 6a–f.

Figure 2A:
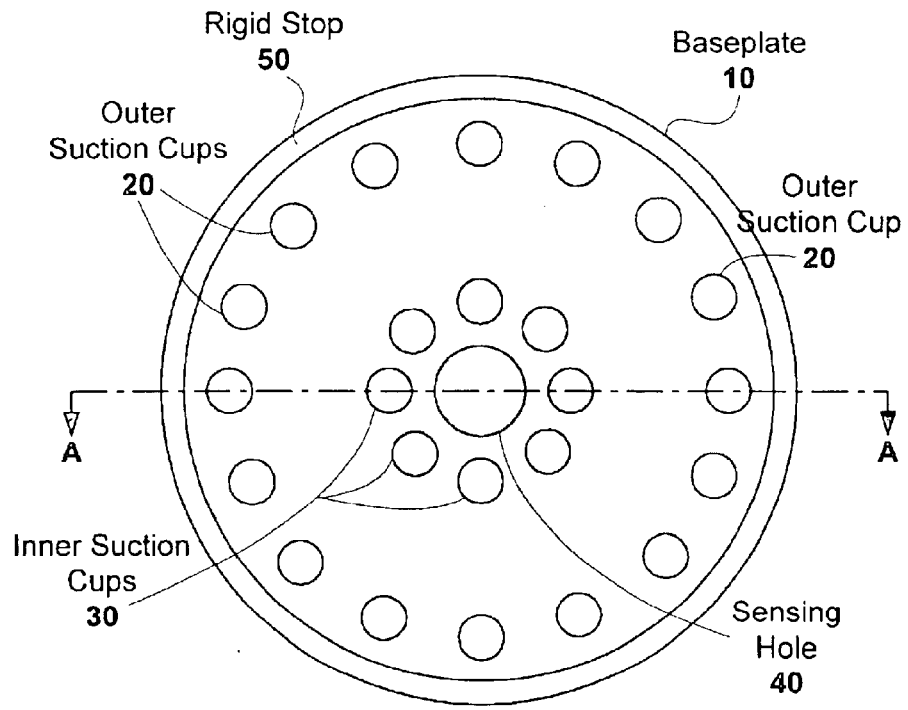
FIG. 2a is a bottom view of a calorimeter mounting scheme configured in accordance with another embodiment of the present invention.
Figure 2B:
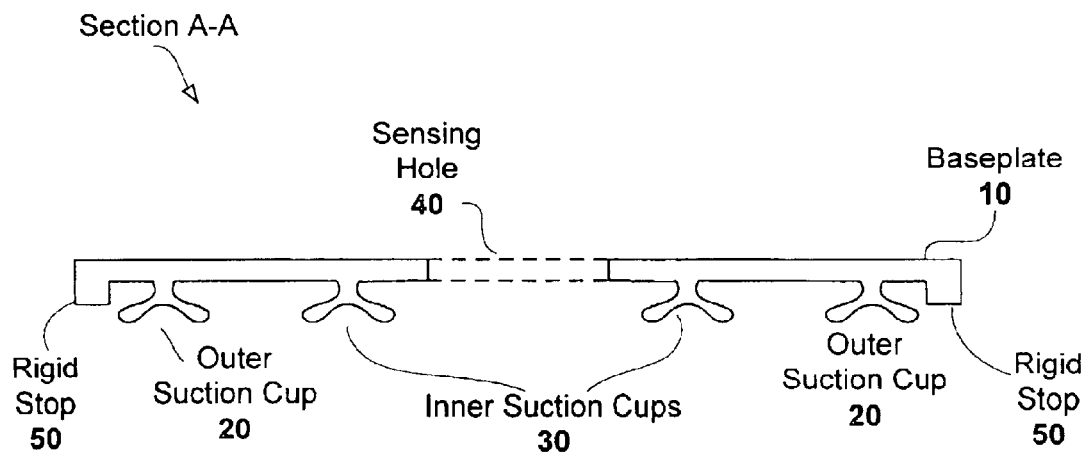

FIGS. 2a and 2b provide respective views of a calorimeter mounting scheme configured in accordance with another embodiment of the present invention. This embodiment is similar to that discussed in reference to FIGS. 1a–b, and further includes a rigid stop 50. In this example, the rigid stop 50 is a ring-shaped ridge disposed on the outer perimeter of the baseplate 10. The stop 50 helps to establish a pre-set distance of the colorimeter device to the target screen, and has its height set accordingly (so that the suction cups of the array can be fully seated). The stop 50 can be, for example, formed as an integral part of the suction cup array using injection molding techniques as previously described.

Alternatively, the stop 50 can be a separate part, such as a pre-formed rubber ring having suitable dimensions. This separate part can be operatively coupled to the array of suction cups using conventional bonding or attachment techniques. Note that the configuration of the stop 50 can vary. For example, the location of the stop 50 can be between the inner and outer suction cup rings. Alternatively, or in addition to, the stop 50 can be a series of shorter segments or a set of strategically placed posts rather than a continuous ring. Also, the shape of stop 50 can vary (e.g., rectangular or square). So long as the stop 50 operates to establish the distance of the mountable device to the target screen.

FIGS. 3a and 3b provide respective views of a colorimeter mounting scheme configured in accordance with another embodiment of the present invention. This embodiment is similar to that discussed in reference to FIGS. 1a–c, and further includes a sensor shield 60. In this example, the sensor shield 60 is a ring-shaped ridge disposed on the outer perimeter of the sensing hole 40. The shield 60 operates to shield the sensors of the colorimeter from extraneous light or light noise generated by sources other than the target source being measured, and has its height set accordingly (so that the suction cups of the array can be fully seated). The shield 60 should be supple enough so as to yield when it contacts the target surface, thereby forming an effective light seal.

The shield 60 can be, for example, formed as an integral part of the suction cup array using injection molding techniques as previously described. Alternatively, the shield 60 can be a separate part, such as a pre-formed rubber ring having suitable dimensions. This separate part can be operatively coupled to the array of suction cups using conventional bonding or attachment techniques.

FIG. 4 is a bottom view of a colorimeter mounting scheme configured in accordance with another embodiment of the present invention. As can be seen, the array of suction cups can be formed from many diverse patterns. Here, baseplate 10 is rectangular shaped, and has a sensing hole that is off-center. The outer suction cups 20 are disposed proximate the outer perimeter of the baseplate 10, while the inner suction cups 30 are disposed about the sensing hole 40. Additional features of this particular embodiment include a rigid stop 50 in two distinct locations (50a and 50b), and a sensing shield 60 that is provided about the sensing hole 40.

Rigid stop 50a is disposed in a rectangular shape on the elongated side of the baseplate 10, while 50b is disposed in a line shape between the sensing hole and the adjacent side. As previously stated, the purpose of the rigid stop 50a/b is to establish a preset distance of the colorimeter device to the target screen. Its height is set so that the suction cups of the array can be fully seated. The sensor shield 60 operates to shield the sensors of the colorimeter from extraneous light, and has a height substantially equal to or slightly taller than that of the stops 50a/b. Note that the sensor shield 60 can be made more supple (e.g., because it is narrower) than the stops 50a/b. This will allow for a robust seal to prevent extraneous light from entering the sensor area. This shielding feature aids a sensor in its ability to measure very small levels of light at high accuracy since only light from the target is measured.

Note that this entire structure can be formed by injection molding techniques as previously discussed. Alternative embodiments may be fabricated using separate parts (e.g., separate shield 60 and stops 50a–b) that are bonded or otherwise operatively coupled to form the overall structure. Further note that the previous discussion as to the various levels of integration and configurations of the baseplate 10, suction cup array, and colorimeter housing equally apply here.

Figure 5:
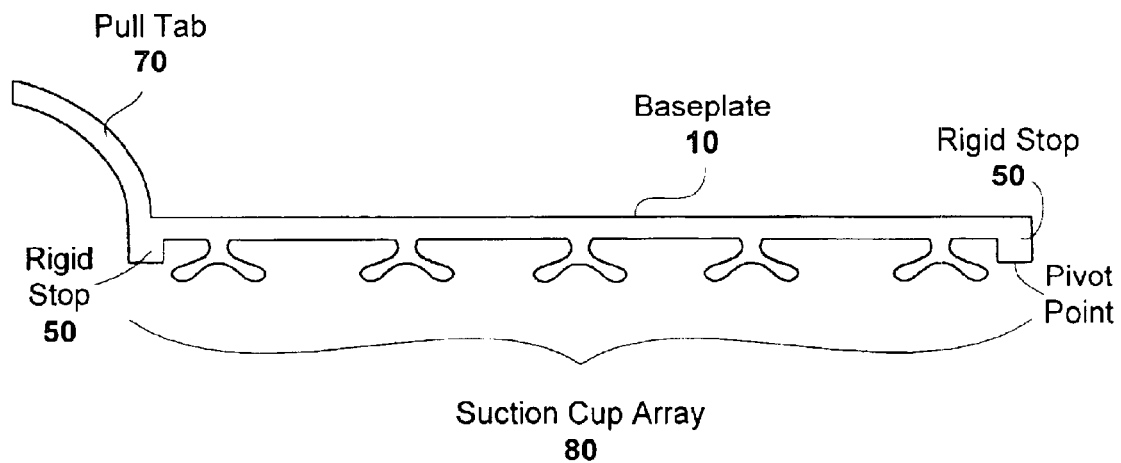
FIG. 5 is a cross-section view of a calorimeter mounting scheme configured in accordance with another embodiment of the present invention.

FIG. 5 is a cross-section view of a calorimeter mounting scheme configured in accordance with another embodiment of the present invention. This particular embodiment includes a pull-tab 70 that is integrally formed or otherwise operatively coupled to a suction cup array 80. The tab 70 is of sufficient size so as to allow an operator to grip and pull the tab during the removal process. Assuming a rigid design (where the baseplate/array configuration will generally not bend), a pivot point is defined at the end opposite the pull tab 70. Here, note that the pivot point is effectively part of the rigid stop 50, and enables a cantilever effect in conjunction with an operator pulling the tab 70 during the removal process.

As discussed in reference to other embodiments, the suction cup array 80 is formed or otherwise disposed on the baseplate 10. In general, the suction cups of the array can be placed in any number of patterns to provide optimum force and position control as desired based on the particular application and embodiment. The actual array pattern is based on a number of considerations. For example, the number of suction cups in the array and/or the physical properties of the suction cup material can be varied so that the force to apply and remove the mounting system are suitable, and so that the retention force is capable of carrying the required load (e.g., the weight of the calorimeter assembly). Likewise, the dimensional aspects of the suction cups (e.g., diameter, depth, and thickness of the cups) can be varied so that the forces required to apply and remove are suitable for a given application.

The removal force further depends, for instance, on the rigidness of the design, and in particular, whether the suction cups of the array can be released at least semi-sequentially (assuming a flexible design allowing the mounting system to be peeled off the target surface like a band-aid), or whether the suction cups of the array must be effectively released simultaneously (assuming a rigid design allowing the mounting system to be cantilevered off the target surface). The pull tab 70 arrangement will also impact the removal force, providing greater mechanical advantage. The walls of each cup can generally be thin (e.g., 0.010 to 0.050 inches), and the cup stiffness can therefore be assumed negligible.

The removal force from one suction cup can be estimated by $F = P \cdot A$, where F is the removal force at release (i.e., the time at which the cup seal fails), A is the area to which the force is applied, and P is the pressure differential between the inside and outside of the cup. The area $A = \pi^2 D_A / 4$, where $D_A$ is the cup diameter at the instant of release, an the pressure $P = P_{atm} - P_i$, where $P_{atm}$ is the atmospheric pressure external to the cup and $P_i$ is the pressure internal to the cup. Note that $P_i$ increases toward atmosphere until seal fails at release.

Assuming a rigid mounting system design that is cantilevered off the target surface, the total removal force would be F·N, where F is the removal force for one suction cup and N is the number of cups in the array. This further assumes that each cup is substantially identical and requires approximately the same removal force, F. Note, however, that alternative embodiments of the invention may employ a suction cup array utilizing non-uniform cup diameters.

For example, suction cups at and/or near the pivot point end of the mount can have a larger diameter to provide greater holding power, while suction cups at and/or near the pull tab 70 end of the mount can have a smaller diameter to provide less holding power. The mechanical advantage provided by the cantilever effect will assist in removing the cups with greater holding power. In such a non-uniform embodiment, the total removal force, $\Sigma F$, is $F_1+F_2+F_3 \ldots F_N$, where array has a total of N suction cups, and the individual removal forces of each of the suction cups 1 through N are added.

Dimensional Details of Mounting System

Figure 6A:
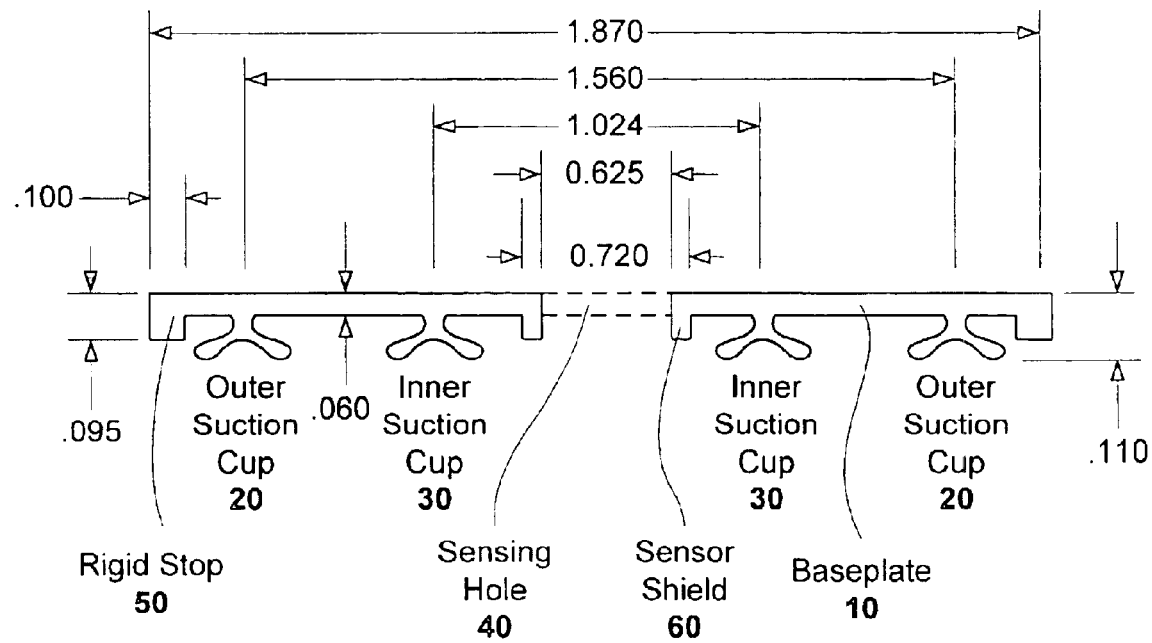
Figure 6B:
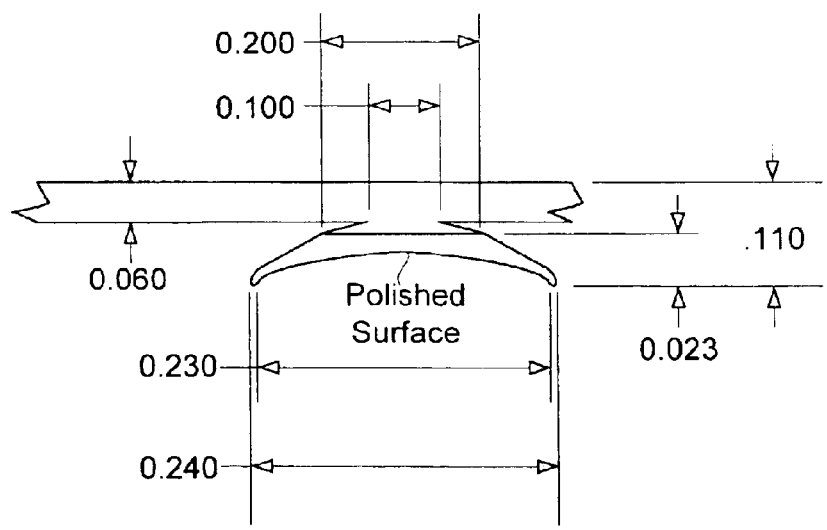

FIG. 6*a* illustrates dimensional details of a colorimeter mounting scheme configured in accordance with one embodiment of the present invention. All noted dimensions are in inches. It will be appreciated that the mounting system configured in accordance with the principles of the present invention can have numerous dimensions, depending on the particulars of a given application, as will be apparent in light of this disclosure. The example dimensions are provided in the name of robust disclosure and to demonstrate one possible embodiment. However, the present invention is not intended to be limited to any one such configuration or embodiment.

Here, the baseplate 10 is round and has an outer ring of suction cups 20 and an inner ring of suction cups 30, such as discussed in reference to FIGS. 1 *a–c*. In addition, the array of suction cups is further configured with a sensing hole 40, a rigid stop 50, and a sensor shield 60 which operate as previously discussed. The outer ring of suction cups 20 includes eighteen evenly spaced cups on a 1.560 bolt circle, while the inner ring of suction cups 30 includes twelve evenly spaced cups on a 1.024 bolt circle. The outer diameter of each cup is about 0.240.

In this particular embodiment, the array of suction cups, including suction cups 20 and 30, the sensing hole 40, and the rigid stop 50, is formed with injection molding techniques using a low viscosity thermoplastic elastomer blend of 96% ALCRYN 2250 UT with 4% ALCRYN 2260 BK by weight. The black color of the BK material renders the UT material nearly opaque. Note that other blends can be used here as well, or a non-blend, such as 100% ALCRYN 2250 UT, which would provide a transparent suction cup array. Note such transparency can be used to eliminate the need for a sensing hole, but may implicate a more involved shielding scheme if shielding is desired. The formed array is bonded to the ABS/PC plastics of a calorimeter housing with LOC-TITE 401 with PRISM primer.

The mold used to make the array has certain qualities that provide desired qualities of the formed array, and facilitate its fabrication. In particular, areas of the mold that correspond to flat, non-suction cup areas of the array are configured with a slightly rough EDM (electric discharge machining) finish. This allows the thermoplastic elastomer material to release from the mold. The mold areas that correspond to the inner bowl area of the suction cups are highly polished, which provides a smooth bowl surface. This assures good vacuum holding power.

Each cup in the array is designed to collapse during ejection from the mold/tool, which helps in getting the array of the tool. Note that these design aspects of the suction cups also control the desired holding force and variation in cup displacement. In more detail, the mold generally has a length, width, and thickness. In addition, many suction cup shapes or "cup sub-molds" are defined in the major front surface of the mold. These sub-molds form the bowl shape of each cup and the narrower cup neck that connects the cup to the major back surface of the array. Thus, the cross-section of a cup's widest diameter is designed to collapse and pull through the smaller neck diameter of the mold, without damaging the formed cup.

The major back surface of the mold can be a removable plate so that the formed array can be accessed after injection and cooling of the material. This detachable major back surface is generally configured with one or more runners for filling the mold with the material. The low viscosity of ALCRYN enables rapid filling of the mold via a single, wide (e.g., one half inch) runner coupled to the center of the back plate. Greater viscosity materials may require multiple runners. In any event, once the rubber or elastomer material is flowed into the mold and cooled, the major back surface of the mold can be removed, so that the array can be peeled out of the mold. Gate material left by runners, as well as other excess material (if any), can be trimmed during secondary operations (e.g., die cut operation to trim excess material and clean array).

Release materials, such as silicon, can be used to aid this removal process. Note that a chemical wash can be used to remove residue of the release material to avoid leaving any such residue on a target surface (e.g., LCD display screen) when the mounting system is deployed.

FIGS. 6*b–f* each show exploded views of a suction cup included in the array. The dimensions are drawn to illustrate various features, and are not drawn to scale. Note that the inner surface of the cup can be highly polished (based on the mold as previously discussed) to provide strong suction capability. Further note that the thickness of each cup can vary within a range, where the thinner wall section is at the widest diameter of the cup, and the thicker wall section is near the neck that couples the cup to the major plane of the array. Here, it can be seen that the formed array releases from the mold/tool by the cup features collapsing within the smallest cross-sectional area of part, which is the neck portion.

Each suction cup has an engaged-state (where the cup is fully seated), a relaxed-state (where the cup is not seated), and a displacement distance. The displacement distance is the distance the cup will move between when transitioning from the engaged-state to the relaxed-state. In accordance with the principles of the present invention, the suction cups of the array are configured to provide a short displacement distance, thereby enabling positional stability. In this particular example, the displacement distance is approximately 0.023 inches or less. The outer cup diameter here is 0.240 inches, and the inner cup diameter is about 0.230 inches. Other embodiments may have a different displacement distances and maximum diameters. An example range of displacement distances is from 0.015 to 0.115 inches, and a range of maximum cup diameter can be 0.250 or less. The goal here is to reduce or otherwise eliminate variation in the mounting distance relative to the target surface.

The foregoing description of the embodiments of the invention has been presented for the purposes of illustration and description. It is not intended to be exhaustive or to limit the invention to the precise form disclosed. Many modifications and variations are possible in light of this disclosure.

It is intended that the scope of the invention be limited not by this detailed description, but rather by the claims appended hereto.

What is claimed is:

1. A mounting system for attaching a colorimeter to a target screen, the system comprising:
   an array of suction cups adapted to hold the colorimeter in position on the target screen, each cup in the array having a maximum displacement distance of 0.115 inches or less, thereby enabling positional stability of the colorimeter, the maximum displacement distance defining a distance any one cup will move in transitioning from a fully engaged-state to a fully relaxed-state;
   a sensor hole located in the array, so as to allow sensors of the colorimeter to receive light emitted from the target screen;
   a sensor shield located about the sensor hole, and adapted to shield sensors of the colorimeter from extraneous light generated by sources other than the target screen;
   a baseplate operatively coupled to the array of suction cups, wherein the baseplate is adapted to be operatively coupled to a housing of the colorimeter or is part of the colorimeter housing;
   one or more rigid stops located on the array, so as to establish a pre-set distance of the colorimeter to the target screen, each stop having a height that allows each of the suction cups to be fully seated.

2. The system of claim 1 wherein the array of suction cups is integral with the baseplate.

3. The system of claim 2 wherein the array of suction cups is bonded to the baseplate.

4. The system of claim 1 wherein a mold is used to make the array of suction cups, and areas of the mold that correspond to flat, non-suction cup areas of the array are configured with a slightly rough EDM finish, thereby facilitating release of the array from the mold.

5. The system of claim 1 wherein the sensor shield is formed as an integral part of the array using injection molding techniques.

6. The system of claim 1 wherein the one or more rigid stops are formed as an integral part of the array using injection molding techniques.

7. The system of claim 1 wherein the array is a single piece of injection moldable elastomer or rubber.

8. The system of claim 1 wherein the array includes an inner group of suction cups and an outer group of suction cups, and is a single piece of injection moldable elastomer or rubber.

9. The system of claim 8 wherein the inner and outer groups of suction cups are each arranged in respective rings, with each group having ten or more suction cups each having a maximum diameter of 0.250 inches or less.

10. The system of claim 1 wherein each suction cup has a maximum cup diameter of 0.250 inches or less.

11. A mounting system for attaching a colorimeter to a target screen at a pre-set distance, the system comprising:
    an injection molded array of suction cups adapted to hold the colorimeter in position on the target screen, and to control both the pre-set distance and variation of distance between the colorimeter and the target screen, the array including an inner group of suction cups and an outer group of suction cups; and
    a sensor shield located about a sensor hole located in the array, and adapted to shield sensors of the colorimeter from extraneous light generated by sources other than the target screen;
    wherein the array includes one or more rigid stops that operate to establish the pre-set distance of the colorimeter to the target screen, each stop having a height that allows each of the suction cups to be fully seated.

12. The system of claim 11 wherein the array, sensor hole, and sensor shield are a single piece of injection moldable elastomer or rubber.

13. The system of claim 11 wherein each cup in the array has a maximum displacement distance of 0.05 inches or less, thereby enabling positional stability of the colorimeter, the maximum displacement distance defining a distance any one cup will move in transitioning from a fully engaged-state to a fully relaxed-state.

14. The system of claim 13 wherein each suction cup has a maximum cup diameter of 0.250 inches or less.

15. The system of claim 11 comprising:
    a baseplate operatively coupled to the array of suction cups, wherein the baseplate is adapted to be operatively coupled to a housing of the colorimeter or is part of the colorimeter housing.

16. The system of claim 15 wherein the baseplate is rigid and the system further includes a pull tab operatively coupled to one end of the baseplate and a pivot point at an opposite end, thereby allowing the mourning system to be cantilevered off of the target screen during removal.

17. A mounting system for attaching a colorimeter to a target screen, the system comprising:
    an array of suction cups adapted to hold the colorimeter position on the target screen, each cup in the array having a maximum displacement distance of 0.115 inches or less, thereby enabling positional stability of the colorimeter, the maximum displacement distance defining a distance any one cup will move in transitioning from a fully engaged-state to a fully relaxed-state;
    a sensor shield located about a sensor hole of the array, and adapted to shield sensors of the colorimeter so that only information received from the target screen is sensed; and
    one or more rigid stops that operate to establish a pre-set distance of the colorimeter to the target screen, each stop having a height that allows each of the suction cups to be fully seated.

18. The system of claim 17 wherein each suction cup has a maximum cup diameter of 0.250 inches or less.

19. The system of claim 17 wherein the array, the sensor shield, and the one or more rigid stops are a single piece of injection moldable elastomer or rubber.

20. The system of claim 17 further comprising: a baseplate operatively coupled to the array of suction cups.

21. The system of claim 20 wherein the baseplate is rigid and the system further includes a pull tab operatively coupled to one end of the baseplate and a pivot point at an opposite end, thereby allowing the mounting system to be cantilevered off of the target screen during removal.

* * * * *